US007513900B2

(12) United States Patent
Carrison et al.

(10) Patent No.: US 7,513,900 B2
(45) Date of Patent: Apr. 7, 2009

(54) APPARATUS AND METHODS FOR REDUCING COMPRESSION BONE FRACTURES USING HIGH STRENGTH RIBBED MEMBERS

(75) Inventors: Harold F. Carrison, Pleasanton, CA (US); Lex P. Jansen, Pleasanton, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 921 days.

(21) Appl. No.: 10/674,723

(22) Filed: Sep. 29, 2003

(65) Prior Publication Data

US 2005/0070911 A1 Mar. 31, 2005

(51) Int. Cl.
*A61B 17/56* (2006.01)
(52) U.S. Cl. .......................................... 606/90; 606/279
(58) Field of Classification Search ................. 132/224, 132/225; 606/246, 259, 261, 279, 300, 326, 606/328; 623/17.11, 17.15
See application file for complete search history.

(56) References Cited

U.S. PATENT DOCUMENTS

| 103,039 | A | * | 5/1870 | Gerecke | 223/35 |
|---|---|---|---|---|---|
| 111,475 | A | * | 1/1871 | Roble | 223/35 |
| 4,135,506 | A | | 1/1979 | Ulrich | |
| 5,059,193 | A | | 10/1991 | Kuslich | |
| 5,171,278 | A | | 12/1992 | Pisharodi | |
| 5,653,763 | A | | 8/1997 | Errico et al. | |
| 5,693,100 | A | | 12/1997 | Pisharodi | |
| 5,702,453 | A | | 12/1997 | Rabbe et al. | |
| 5,723,013 | A | | 3/1998 | Jeanson et al. | |

(Continued)

FOREIGN PATENT DOCUMENTS

| DE | 40 12 622 C1 | 7/1991 |
|---|---|---|
| WO | WO 92/01428 | 2/1992 |

OTHER PUBLICATIONS

PCT International Partial Search Report for PCT/US2004/031379, Applicant: Scimed Life Systems, Inc., Form PCT/ISA/206, dated Feb. 21, 2005 (8 pages).
PCT International Search Report for PCT/US2004/031379, Applicant: Scimad Life Systems, Inc., Forms PCT/ISA/210 and 220, dated Apr. 29, 2005 (8 pages).
PCT Written Opinion of the International Search Authority for PCT/US2004/031379, Applicant: Scimed Life Systems, Inc., Form PCT/ISA/237, dated Apr. 29, 2005 (8 pages).

*Primary Examiner*—Eduardo C Robert
*Assistant Examiner*—David Comstock
(74) *Attorney, Agent, or Firm*—Vista IP Law Group LLP

(57) ABSTRACT

Devices and methods are provided for treating a bone structure (such as, e.g., reducing a bone fracture, e.g., a vertebral compression fracture, or stabilizing adjacent bone structure, e.g., vertebrae) is provided. The device comprises rigid or semi-rigid members, each of which comprises a common base and a plurality of ribs that extent along the a longitudinal portion of the common base. The device is configured to be placed in a collapsed state by engaging the pluralities of ribs of the members in an interposed arrangement, and configured to be placed in a deployed state by disengaging the pluralities of ribs. The ribs can be any shape, e.g., flutes, that allows opposing ribs to intermesh with one another. In this manner, the device has a relatively small profile when placed in the collapsed state, so that it can be introduced through small openings within the bone structure, while preserving the shear strength of the members during deployment of the device.

9 Claims, 13 Drawing Sheets

U.S. PATENT DOCUMENTS

| | | | |
|---|---|---|---|
| 5,776,198 | A | 7/1998 | Rabbe et al. |
| 5,827,328 | A | 10/1998 | Buttermann |
| 6,039,761 | A | 3/2000 | Li et al. |
| 6,056,749 | A | 5/2000 | Kuslich |
| 6,117,174 | A | 9/2000 | Nolan |
| 6,171,307 | B1 | 1/2001 | Orlich |
| 6,193,757 | B1 | 2/2001 | Foley et al. |
| 6,241,769 | B1 | 6/2001 | Nicholson et al. |
| 6,309,421 | B1 | 10/2001 | Pisharodi |
| 6,344,057 | B1 | 2/2002 | Rabbe et al. |
| 6,395,031 | B1 | 5/2002 | Foley et al. |
| 6,582,431 | B1 | 6/2003 | Ray |
| 6,607,530 | B1 | 8/2003 | Carl et al. |
| 6,607,544 | B1 | 8/2003 | Boucher et al. |

* cited by examiner

APPARATUS AND METHODS FOR REDUCING COMPRESSION BONE FRACTURES USING HIGH STRENGTH RIBBED MEMBERS

FIELD OF THE INVENTION

The invention relates to the treatment of bone structures, such as vertebrae, and in particular, to the reduction and stabilization of compression bone fractures.

BACKGROUND OF THE INVENTION

Spinal injuries, bone diseases, such as osteoporosis, vertebral hemangiomas, multiple myeloma, necrotic lesions (Kummel's Disease, Avascular Necrosis), and metastatic disease, or other conditions can cause painful collapse of vertebral bodies. Osteoporosis is a systemic, progressive and chronic disease that is usually characterized by low bone mineral density, deterioration of bony architecture, and reduced overall bone strength. Vertebral compression fractures (VCF) are common in patients who suffer from these medical conditions, often resulting in pain, compromises to activities of daily living, and even prolonged disability.

FIG. 1 illustrates three vertebrae 10, 12, and 14, each with an anterior side 16, a posterior side 18, and lateral sides 20 (only one shown). Vertebrae 10 and 14 are fully intact, while vertebra 12 has a VCF 22 (i.e., the top 24 and bottom 26 of the vertebra 12 have been displaced towards each other). The force required to reduce the VCF 22 (i.e., to displace the top 24 and bottom 26 of the vertebra 12 back to their original positions) can often be rather high. Present needles for use within vertebrae bend or deform in the presence of lateral force, and thus, are not rigid enough to reduce VCF's. Balloons can be placed in the fractured vertebra and expanded to reduce the VCF. Such balloons, however, will expand equally in all radial directions, which can cause the vertebra to shatter on the anterior, posterior, and lateral sides.

Consequently, there is a significant need to provide an improved means for reducing compression bone fractures, e.g., VCF's.

SUMMARY OF THE INVENTION

In accordance with a first aspect of the present invention, a device for reducing a bone fracture, e.g., a vertebral compression fracture, is provided. The device comprises a first rigid member having a first common base and a first plurality of ribs extending along at least a longitudinal portion of the first common base, and second rigid member having a common base and a second plurality of ribs extending along at least a longitudinal portion of the second common base. The device is configured to be placed in a collapsed state by engaging the first and second pluralities of ribs in an interposed arrangement, and configured to be placed in a deployed state by disengaging the first and second pluralities of ribs. The ribs can be any shape, e.g., flutes, that allows opposing ribs to intermesh with one another. In one preferred embodiment, a coupling mechanism, e.g., a hinge, couples the first and second rigid members together.

The first and second rigid members, when the device is in the collapsed state, can have a combined cross-sectional profile that is substantially the same as each of the individual cross-sectional profiles of the first and second rigid members, when the device is in the deployed state. For example, the combined cross-sectional profile can be circular, and the individual cross-sectional profiles can have an arcuate shape, in which case, the radius of the circular profile can be substantially equal to the radius of curvature of each of the individual cross-sectional profiles. Thus, it can be appreciated that the interposition of the ribs provides a smaller combined profile for the members, while not substantially reducing the shear strength of the individual members during deployment of the device.

In accordance with a second aspect of the present inventions, a method of treating a bone structure having opposing sides and a compression fracture therebetween (e.g., a vertebral compression fracture) is provided. The method comprises placing the previously described device in a collapsed state by engaging the ribs of the respective first and second members in an interposed arrangement, and then introducing the device within the bone structure while in the collapsed state. The method further comprises placing the device in a deployed state by disengaging the ribs of the respective first and second members and moving the first and second members in opposite directions to displace the opposing sides of the bone structure in opposite directions. Preferably, the device is deployed until the compression fracture has been completely reduced. In one preferred method, the device is placed in the respective collapsed and deployed states by hinging the first and second members relative to each other. A treatment medium can be optionally introduced into the bone structure.

In accordance with a third aspect of the present inventions, a device for reducing a bone fracture, e.g., vertebral compression fracture, is provided. The device comprises first and second proximal member portions, and first and second distal member portions. The first proximal and distal member portions can either form a single member or multiple members, and the second proximal and distal member portions can likewise either form a single member or multiple members. The device further comprises a first intermediate hinge located between the respective proximal and distal member portions, wherein a first hinge point is formed, and a second intermediate hinge located between the respective proximal and distal member portions, wherein a second hinge point is formed. If the member portions are formed of single members, the intermediate hinges can be living hinges (i.e., points where the members bend or deform).

The device further comprises an actuating coupling assembly configured for displacing the proximal ends of the first and second proximal member portions and distal ends of the first and second distal member portions towards each other, whereby the first and second hinge points are respectively displaced outward away from each other to deploy the device. In this manner, the device can be used to apply opposing forces on the bone structure in order to reduce the fracture. In an alternative embodiment, the coupling assembly is configured for displacing the proximal ends of the first and second proximal member portions and the distal ends of the first and second distal member portions away from each other, whereby the first and second hinge points are respectively displaced inward towards each other to collapse the device.

In one preferred embodiment, the coupling assembly comprises a drive shaft, a proximal coupling mechanism rotatably coupled to the drive shaft, and a distal coupling mechanism coupled to the drive shaft. In this case, the device further comprises proximal hinges between the respective proximal member portions and the proximal coupling mechanism, and distal hinges between the respective distal members portions and the distal coupling mechanism. The drive shaft can be variously configured. For example, the drive shaft can be a drive screw, in which the proximal coupling mechanism may comprise a nut in which the drive screw is threadedly engaged. Or the drive shaft may be a shear wire, in which case, the proximal coupling mechanism is an annular ring through which the shear wire is slidably engaged. In the case of a shear wire, a weakened region can be provide that causes the shear wire to break off after deployment of the device. The distal coupling mechanism can be, e.g., a spherical cap that houses the distal end of the drive shaft.

The device may optionally include more intermediate hinges to provide a larger surface that contacts the bone structure. For example, the device may comprise a first central member portion located between the first proximal and distal member portions, and a second central member portion located between the second proximal and distal member portions. In this case, the first intermediate hinge will be located between the first proximal member portion and the first central member portion, and the second intermediate hinge will be located between the second proximal member portion and the second central member portion. A third intermediate hinge will be located between the first distal member portion and the first central member portion, and a fourth intermediate hinge will be located between the second distal member portion and the second central member portion. Thus, the first and second central member portions will be respectively displaced outward away from each to deploy the device, thereby providing a greater surface area in contact with the bone structure.

To ensure proper placement and orientation of the member portions, a cannula that is capable of engaging the actuating coupling assembly can be provided. In addition, a driver can be provided in order to operate the actuating coupling assembly. The members can optionally comprise ribs, as previously discussed above, in order to provide a smaller combined profile, while preserving shear strength.

BRIEF DESCRIPTION OF THE DRAWINGS

The drawings illustrate the design and utility of preferred embodiment(s) of the invention, in which similar elements are referred to by common reference numerals. In order to better appreciate the advantages and objects of the invention, reference should be made to the accompanying drawings that illustrate the preferred embodiment(s). The drawings, however, depict the embodiment(s) of the invention, and should not be taken as limiting its scope. With this caveat, the embodiment(s) of the invention will be described and explained with additional specificity and detail through the use of the accompanying drawings in which.

DETAILED DESCRIPTION OF THE PREFERRED EMBODIMENTS

Figure 1:
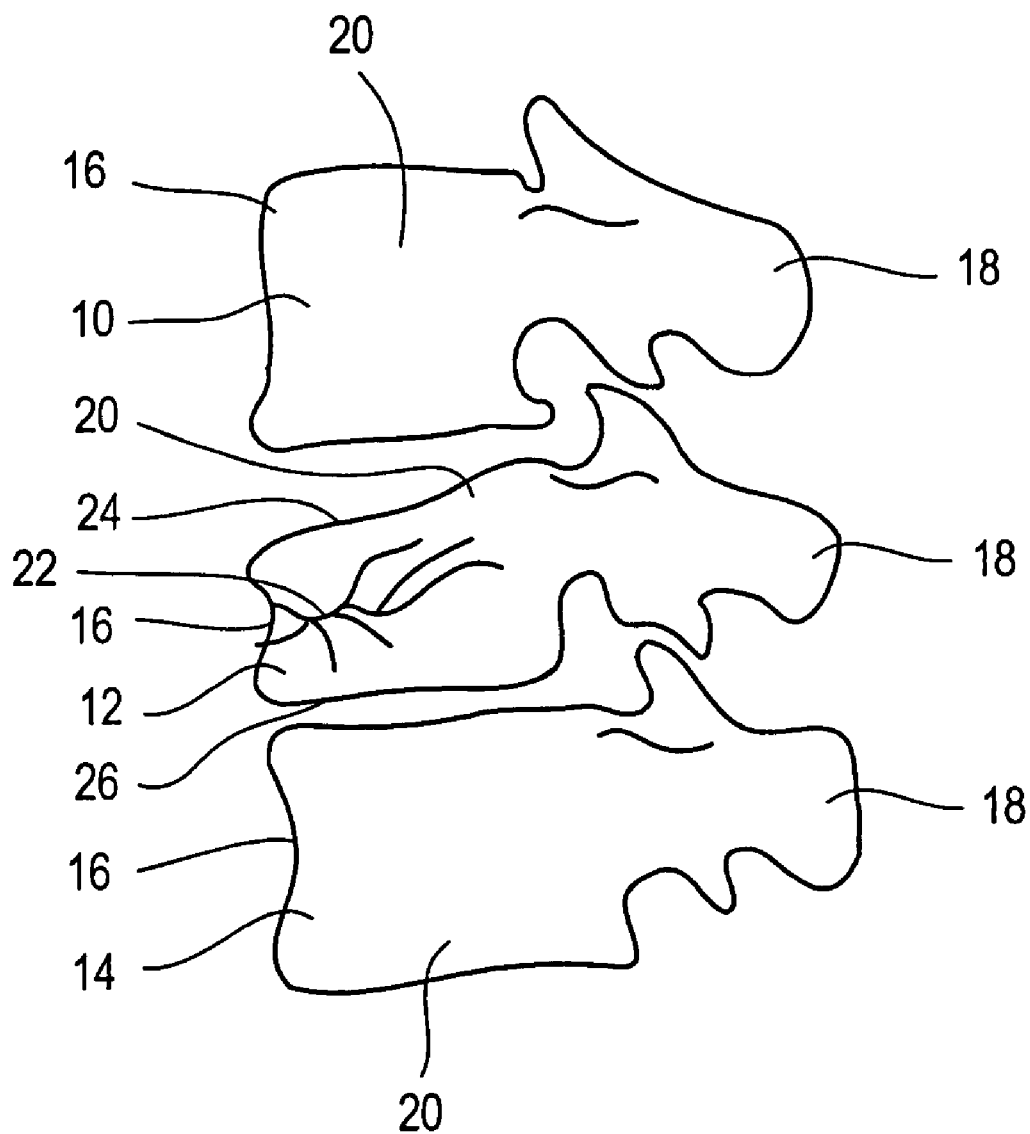
FIG. 1 is a lateral view of three vertebra, two of which are normal, and one of which has a compression fracture.
Figure 2:
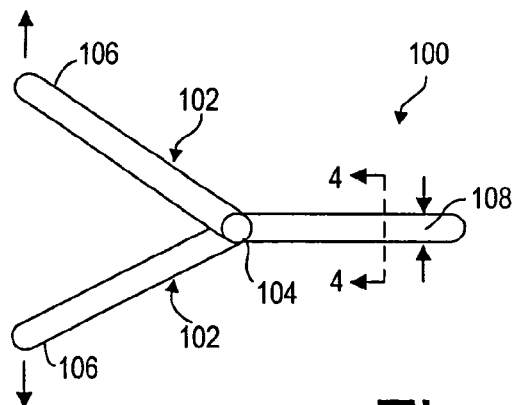
FIG. 2 is a plan view of a vertebral compression fracture reduction device constructed in accordance with a preferred embodiment of the present inventions, wherein the device is particularly shown in a collapsed state.
Figure 3:
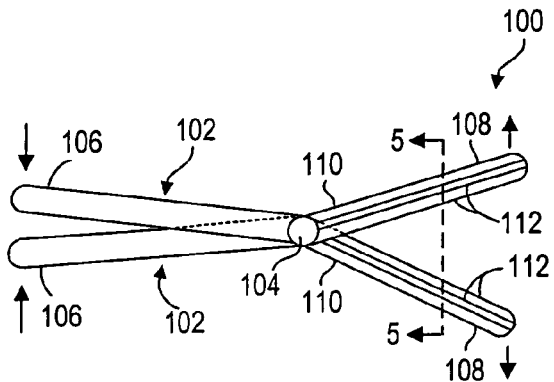
FIG. 3 is a plan view of the device of FIG. 2, wherein the device is particularly shown in a deployed state.

Referring to FIGS. 2 and 3, a bone fracture reduction device 100 constructed in accordance with one preferred embodiment of the present inventions is illustrated. The device 100 can be used for treating a compression bone fracture, and specifically, a compression fracture 202 within a vertebra 200 (shown in FIGS. 7-9). The device 100 generally comprises a pair of rigid members 102, and a coupling mechanism, and specifically a hinge 104, for coupling the members 102 together.

The materials used in constructing the members 102 may comprise any of a wide variety of biocompatible materials. In a preferred embodiment, a radiopaque material, such as metal (e.g., stainless steel, titanium alloys, or cobalt alloys) or a polymer (e.g., ultra high molecular weight polyethylene) may be used, as is well known in the art. Polymethylmethacrylate (PMMA) can also be used if, e.g., the device 100 or portion thereof is to be implanted within the vertebra 200.

Each member 102 has a portion 106 that is proximal to the hinge 104, and a portion 108 that is distal to the hinge 104. As illustrated in FIG. 2, the device 100 can be placed in a collapsed state by displacing the respective proximal member portions 106 away from each other, thereby displacing the respective distal member portions 108 toward each other. As will be described in further detail below, placing the device 100 in a collapsed state facilitates introduction of the distal member portions 108 into the vertebra 200.

In contrast, as illustrated in FIG. 3, the device 100 can be placed in a deployed state by displacing the respective proximal member portions 106 toward each other, thereby displacing the respective distal member portions 108 away from each other. As will be described in further detail below, placing the device 100 in an expanded state causes the distal member portions 108 to create a vertical force that reduces the compression fracture 202 within the vertebra 200. As illustrated, the members 102 are angled, such that the device 100 can be fully deployed without interference between the proximal member portions 106.

The distal member portions 108 are specially designed, such that they can be introduced through smaller channels within the vertebra 200 (e.g., through an 11 gauge channel drilled into the bone), without significant loss of shear strength in the direction of their movement. Notably, the smaller the hole through which the device 100 is introduced, the less trauma is caused to the region.

Figure 4:
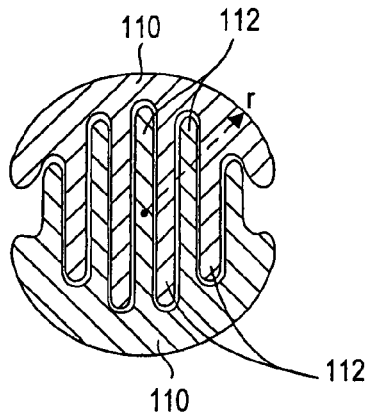
FIG. 4 is a cross-sectional view of the device of FIG. 2, taken along the lines 4-4.
Figure 5:
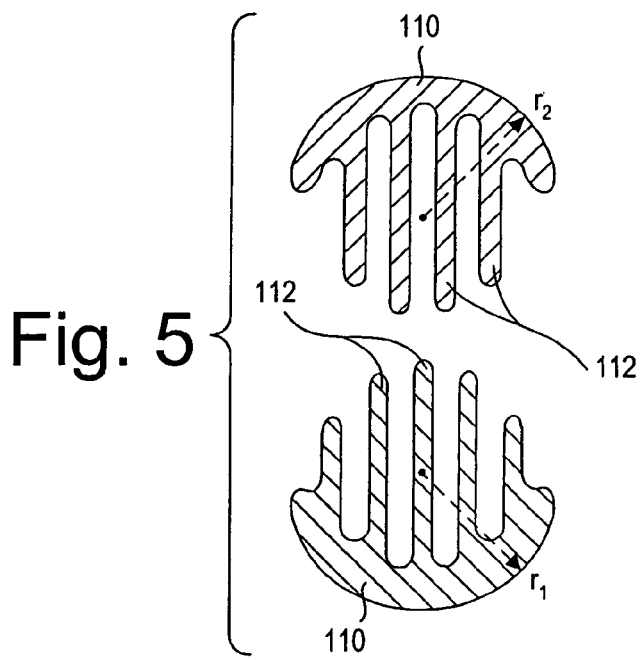
FIG. 5 is a cross-sectional view of the device of FIG. 3, taken along the lines 5-5.

To this end, each member 102 comprises a common base 110 and a plurality of ribs 112 (specifically, flutes) extending along the length of the common base 110, as best shown in FIGS. 4 and 5. As illustrated, the ribs 112 of the respective members 102 are configured to engage each other in an interposed arrangement when the device 100 is placed into the collapsed configuration (FIG. 4), and are configured to disengage each other when the device 100 is placed into the deployed state (FIG. 5). In this manner, the combined cross-sectional profile of the members 102 can be reduced when the device 100 is placed in the collapsed state, thereby minimizing the size of the channel needed to introduce the device 100 within the vertebra 200.

Specifically, the combined cross-sectional profile of the members 102 is about the same as the individual cross-sectional profiles of the members 102 when the device 100 is placed in the deployed state. As can be seen, the combined cross-sectional profile is a circle having a radius r, and the individual cross-sectional profiles are circles having radii $r_1$, $r_2$, wherein the radius r is approximately equal to the radii $r_1$, $r_2$.

Although the combined cross-sectional profile of the members 102 is reduced when the device 100 is placed in the collapsed state, the shear strength of each member 102 is not substantially reduced when the device 100 is placed in the deployed state. Specifically, the ribs 112 support the members 102 along the direction in which shear forces will be applied during deployment of the device 100. In essence, the members 102 have almost the same amount of shear strength as if they were composed of a solid piece of material.

Figure 6:
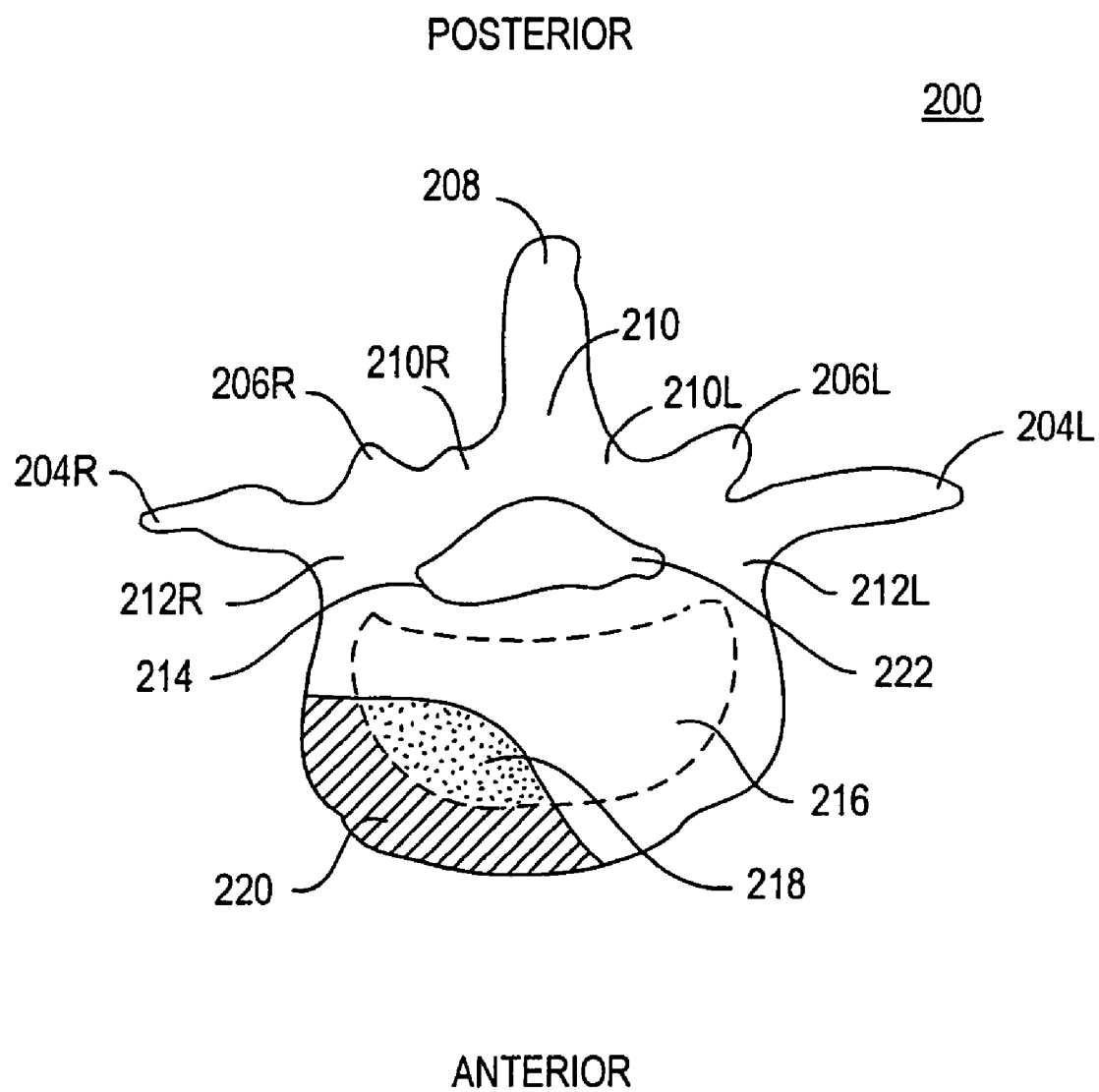
FIG. 6 is a partially cut-away top view of a lumbar vertebra.

Although, as noted above, use of the bone fracture treatment device 100 is not limited to treatment of vertebral ailments, such procedures are discussed here for exemplary purposes. Before discussing such methods of operation, various portions of the vertebra are briefly discussed. Referring to FIG. 6, the posterior of the vertebra 200 includes right and left transverse processes 204R, 204L, right and left superior articular processes 206R, 206L, and a spinous process 208. The vertebra 200 further includes a centrally located lamina 210 with right and left lamina 210R, 210L, that lie in between the spinous process 208 and the superior articular processes 206R, 206L. Right and left pedicles 212R, 212L are positioned anterior to the right and left transverse processes 204R, 204L, respectively. A vertebral arch 214 extends between the pedicles 212 and through the lamina 210. The anterior of the vertebra 200 includes a vertebral body 216, which joins the vertebral arch 214 at the pedicles 212. The vertebral body 216 includes an interior volume of reticulated, cancellous bone 218 enclosed by a compact cortical bone 220 around the exterior. The vertebral arch 214 and vertebral body 216 make up the spinal canal, i.e., the vertebral foramen 222, which is the opening through which the spinal cord and epidural veins pass.

Figure 7A:
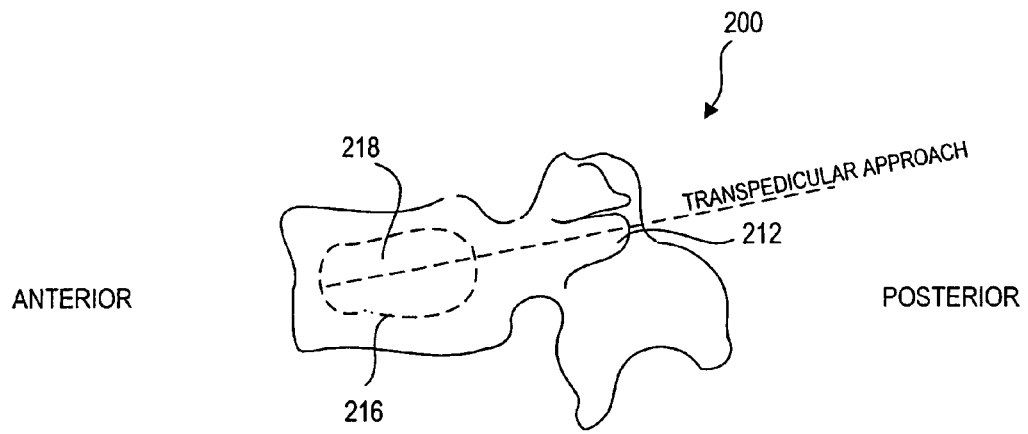
FIG. 7A is a lateral view of posterior transpedicular access route to the anterior vertebral body shown in FIG. 6.
Figure 7B:
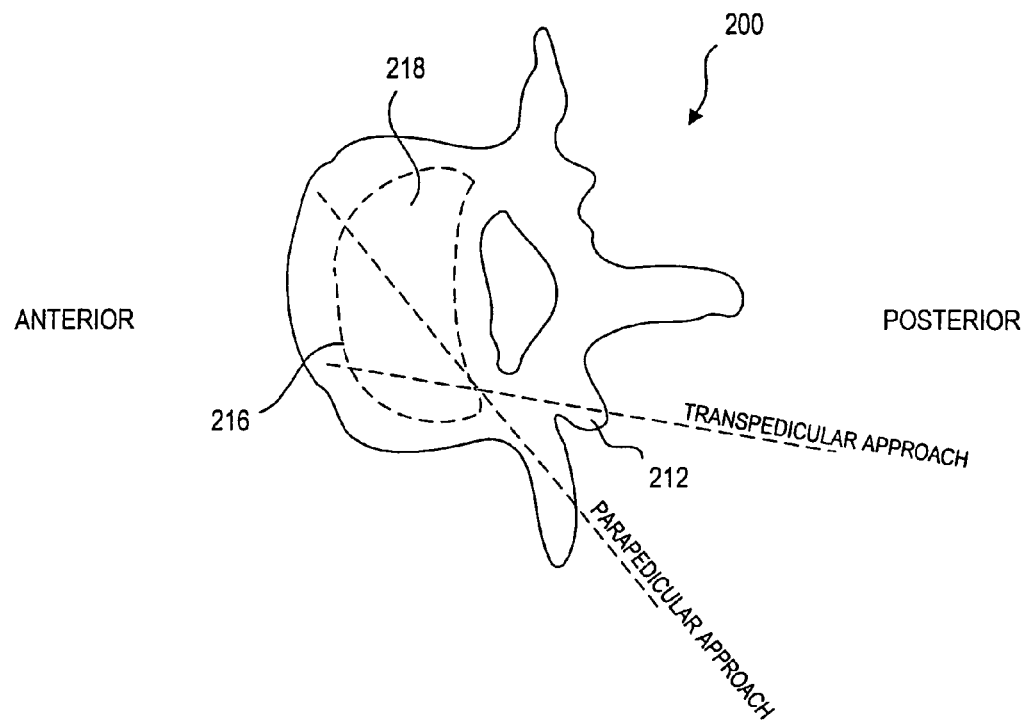
FIG. 7B is a top view of posterior transpedicular and parapedicular access routes to the anterior vertebral body shown in FIG. 7.
Figure 8:
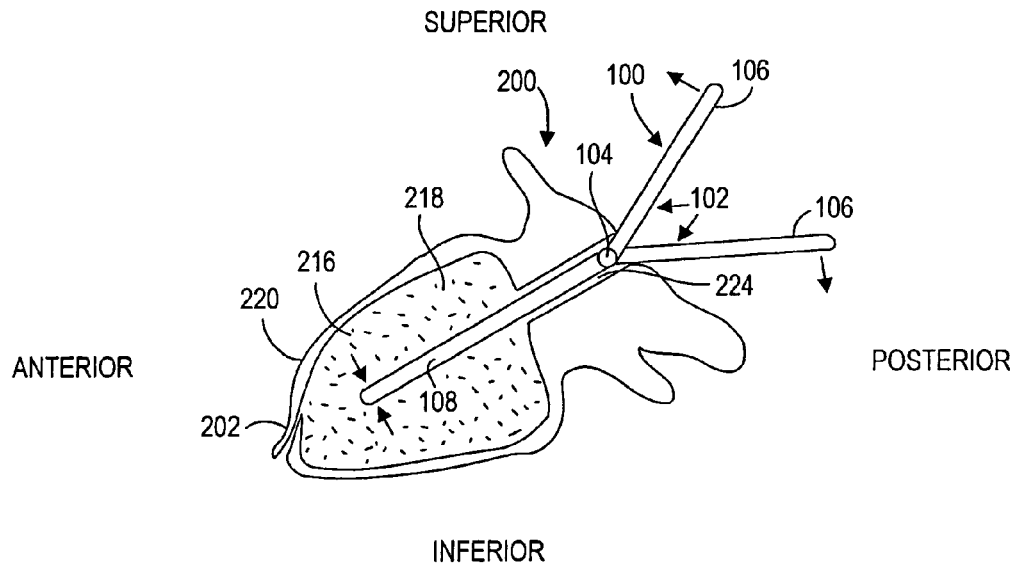
FIGS. 8 and 9 are lateral views of a method of using the device of FIG. 2 to treat a vertebral compression fracture.
Figure 9:
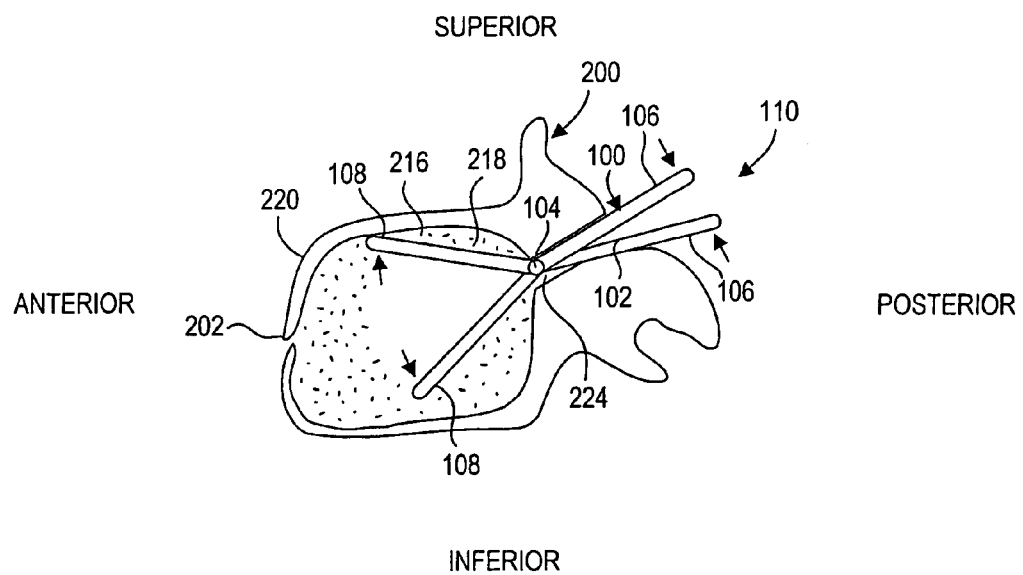

Referring now to FIGS. 7-9, a method of using the device 100 to treat a compression fracture 202 within a vertebra 200 will now be described. First, the physician accesses the interior of the vertebral body 216 by boring a channel or passage 224 into the vertebra 200 using any one of a variety of known means. For example, as depicted in FIG. 7A, in a transpedicular approach, access to the cancellous bone 218 in the vertebral body 216 is gained through the pedicles 212. Alternatively, as depicted in FIG. 7B, a parapedicular approach may be used in which access is gained through the side of the vertebral body 216 beside the pedicles 212. This approach may be selected if the compression fracture 202 has resulted in the collapse of the vertebral body 216 below the plane of the pedicles 212. Still other physicians may opt for an intercostals approach through the ribs (not shown) or a more clinically challenging anterior approach (not shown) to the vertebral body 216.

Once access to the cancellous bone 218 in the vertebral body 216 has been accessed, the physician places the device 100 in the collapsed state by displacing the proximal portions 106 of the respective members 102 away from each other, thereby collapsing the distal portions 108 of the respective members 102 about the hinge 104 and upon each other until the ribs 112 of the respective members 102 have been fully engaged. The distal member portions 108 can then be introduced through the passage 224 and into the cancellous bone 218, as illustrated in FIG. 8. The hinge 104 of the device 100 may be positioned at the proximal end of the passage 224 in order to provide the proximal member portions 106 clearance to spread apart. The device 100 is oriented, such that movement of the distal member portions 108 will be in a direction perpendicular to the superior and inferior sides of the vertebra 200.

After proper orientation, the physician places the device 100 in the deployed state by displacing the proximal member portions 106 about the hinge 104 toward each other, thereby expanding the distal member portions 198 away from each other—in effect, disengaging the ribs 112 of the respective members 102 from each other. As a result, movement of the distal member portions 108 in opposite directions will in turn compress the cancellous bone 218 against the cortical bone 220, thereby displacing the superior and inferior sides of the vertebra 200 in opposite directions to reduce the compression fracture 202, as illustrated in FIG. 9. In performing this step, the device 100 may be advanced distally in order to position the hinge 104 at the distal end of the passage 224, thereby providing the proximal member portions 108 clearance to spread apart.

It should be noted that initial movement of the superior and inferior sides of the vertebra 200 will depend upon the nature and age of the compression fracture 202. For example, if the compression fracture 202 is relatively new, it will take a relatively small amount of force to displace the superior and inferior sides of the vertebra 200 in opposite directions. In this case, the compression fracture 202 may immediately begin to reduce in response to the deployment of the device 100. If on the other hand the compression fracture 202 is relatively old, and thus partially fused, it will take a relatively large amount of force to displace the superior and inferior sides of the vertebra 200 in opposite directions. In this case, the compression fracture 202 may only begin to reduce in response to movement of the distal member portions 108 directly against the cortical bone 220, e.g., when the device 100 is substantially deployed.

Thus, it can be appreciated that the provision of ribs 112 on the distal member portions 108 allows the device 100 to be collapsed enough to be introduced through the small passage 224, yet maintain the shear strength necessary to reduce the compression fracture 202.

After reduction of the compression fracture 202 has been completed, the device 100 can be removed from the vertebral body 216, and a therapeutic medium can be introduced through the passage 224 into the void created by displacing the cancellous bone 218 against the cortical bone 220. This can be accomplished using suitable means, such as with a cannula and plunger assembly (not shown). The treatment medium may include granular implants or particles, such as "calcium salts," including Amorphous Calcium Phosphate (ACP), Tricalcium Phosphate (TCP), and $CaSO_4$, $CaPO_4$, Hydroxylapatite (HA), Calcium Aluminate, etc. The treatment medium may also include bone cement, such as PMMA or the like, and other biomaterials, such as donor tissue. The implants or particles or granules within the treatment medium may have approximately the same size, or alternatively, may have a distribution of sizes. The cured therapeutic medium will ultimately provide increased structural integrity for the vertebra 200.

Alternatively, rather than removing the entire device 100 from the vertebral body 216, the device 100 can be left within the vertebral body 216, while the therapeutic medium is introduced into the vertebral body 216 through another passage. In this manner, the reduced fracture can be maintained while the therapeutic medium cures, after which the portion of the device 150 remaining outside of the vertebra 200 can be sheared off. The channel 224 can then be filled with bone cement.

Figure 10:
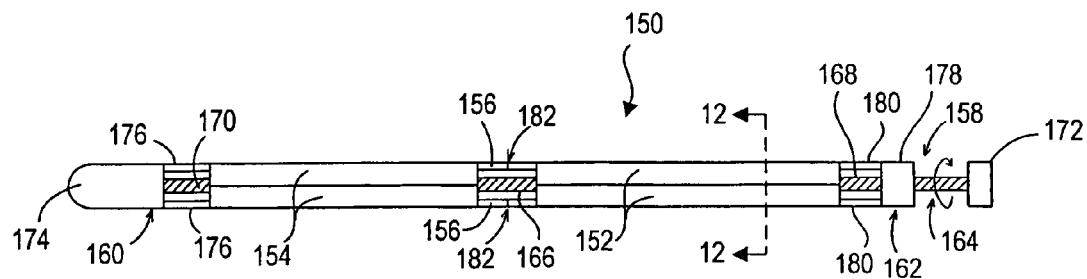
FIG. 10 is a plan view of a vertebral compression fracture reduction device constructed in accordance with another preferred embodiment of the present inventions, wherein the device is particularly shown in a collapsed state.
Figure 11:
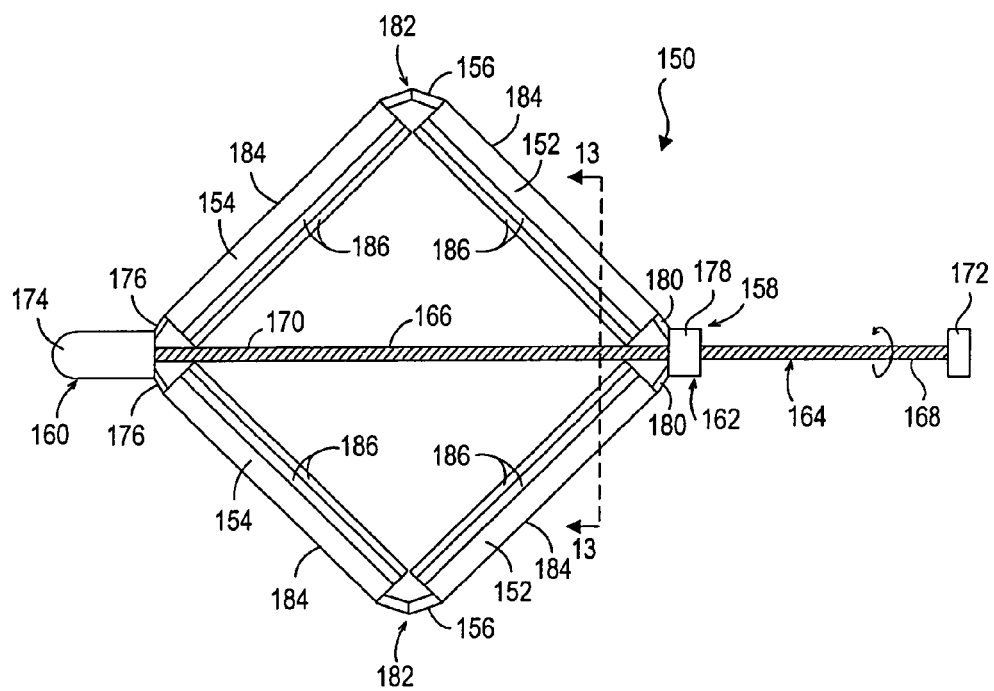
FIG. 11 is a plan view of the device of FIG. 10, wherein the device is particularly shown in a deployed state.

Referring to FIGS. 10 and 11, another bone fracture reduction device 150 constructed in accordance with one preferred embodiment of the present inventions is illustrated. The device 150 can be used for treating a compression bone fracture, and specifically, a compression fracture 202 within a vertebra 200 (shown in FIGS. 14 and 15). The device 150 can be especially used on patients with a relatively large amount of tissue between the skin and the vertebra, because all actuation is accomplished within the vertebra itself. The device 150 generally comprises a pair of proximal rigid members 152, a pair of distal rigid members 154, a pair of intermediate coupling mechanisms (specifically, hinges 156) coupling the proximal members 152 to the distal members 154, and an actuating coupling assembly 158 for alternatively placing the device 150 in a collapsed state and a deployed state, as will be described in further detail below.

The materials used in constructing the proximal and distal members 152/154 may comprise any of a wide variety of rigid biocompatible materials. In a preferred embodiment, a radiopaque material, such as metal (e.g., stainless steel, titanium alloys, or cobalt alloys) or a polymer (e.g., ultra high molecular weight polyethylene) may be used, as is well known in the art. PMMA can also be used if, e.g., the device 150 or portion thereof is to be implanted within the vertebra 200.

The actuating coupling assembly 158 generally comprises a distal coupling assembly 160, a proximal coupling assembly 162, and a drive 164 that interacts with the coupling assemblies 160 and 162. Specifically, the drive 164 comprises a threaded drive shaft or drive screw 166 having a proximal end 168 and a distal end 170, and a drive coupling 172 mounted to the proximal end 168 of the drive screw 166. The distal coupling assembly 160 comprises a hollow spherical cap 174 in which the distal end 170 of the drive screw 166 freely rotates, and a pair of hinges 176 that are coupled to the respective distal ends of the distal members 154. The proximal distal coupling assembly 162 comprises a nut 178 through which the drive screw 166 extends, and a pair of hinges 180 that are coupled to the respective proximal ends of the proximal members 152. Because the drive screw 166 is threaded, the nut 178 (which is also threaded) will be longitudinally displaced in the distal direction towards the spherical cap 174 when the drive screw 166 is rotated in one direction, and will be longitudinally displaced in the proximal direction away from the spherical cap 174 when the drive screw 166 is rotated in the other direction.

In response to distal displacement of the nut 178 relative to the spherical cap 174, the hinging action of the intermediate hinges 156, distal hinges 176, and proximal hinges 180 will cause the pair of proximal members 152 and the pair of distal members 154 to move towards each other—in effect collapsing upon each other, which will then cause the distal ends of the proximal members 152 and the proximal ends of the distal members 154 to move outward (i.e., away from the drive screw 166) at central hinge points 182, thereby placing the device 150 in its deployed state (FIG. 11). In contrast, in response to proximal displacement of the nut 178 relative to the spherical cap 174, the hinging action of the intermediate hinges 156, distal hinges 176, and proximal hinges 180 will cause the pair of proximal members 152 and the pair of distal members 154 to move away from each other at the central hinge points 182, which will then cause the distal ends of the proximal members 152 and the proximal ends of the distal members 154 to move inward (i.e., towards the drive screw 166), thereby placing the device 150 in its collapsed state (FIG. 10).

Figure 12:
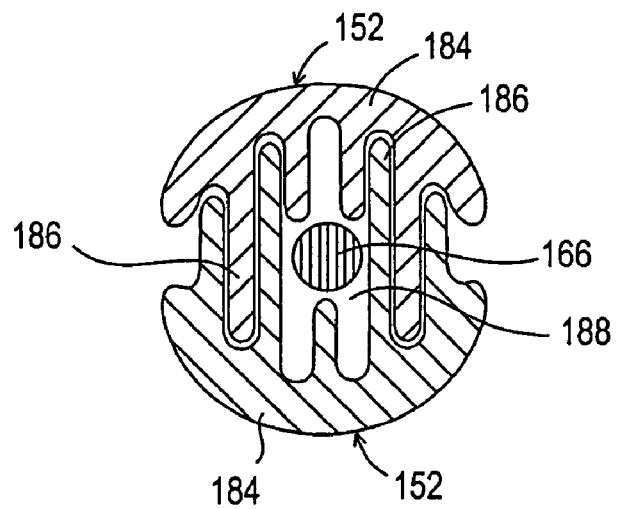
FIG. 12 is a cross-sectional view of the device of FIG. 10, taken along the lines 10-10.
Figure 13:
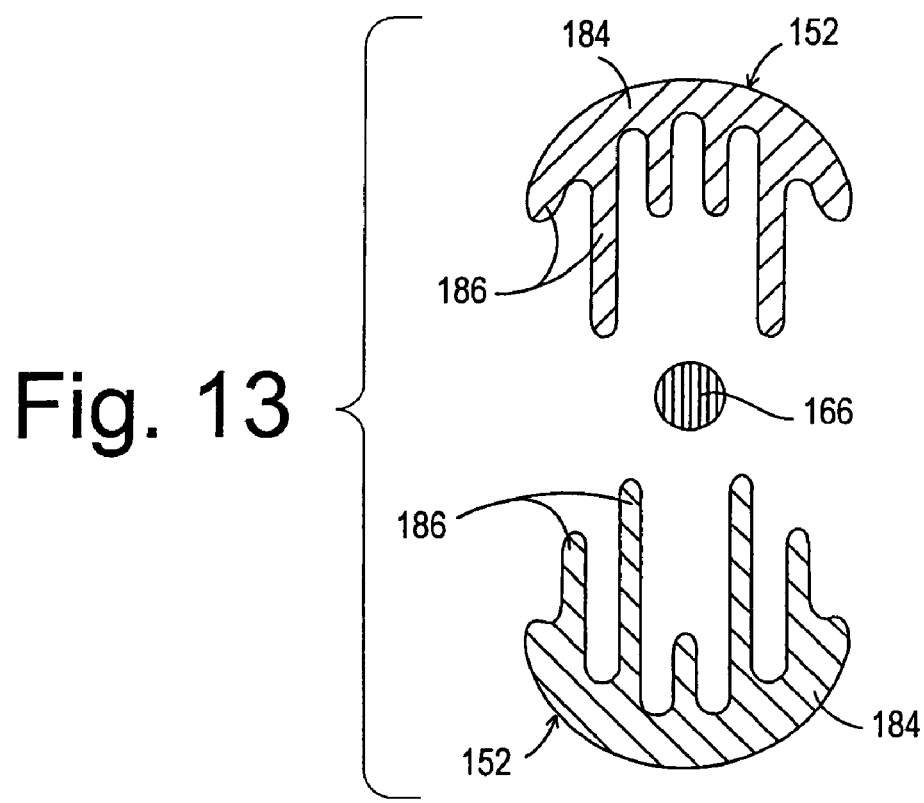
FIG. 13 is a cross-sectional view of the device of FIG. 11, taken along the lines 11-11.

Like with the previously described members of the device 100, the proximal and distal members 154 of the device 150 are specially designed, such that they can be introduced through smaller channels within the vertebra 200 without significant loss of shear strength in the direction of their movement. To this end, each proximal member 152 comprises a common base 184 and a plurality of ribs 186 (specifically, flutes) extending along the length of the common base 184, as best shown in FIGS. 12 and 13. As illustrated, the ribs 186 of the proximal members 152 are configured to engage each other in an interposed arrangement when the device 150 is placed into the collapsed configuration (FIG. 12), and are configured to disengage each other when the device 150 is placed into the deployed state (FIG. 13). As illustrated, the distal ends of some of the ribs 186 have been removed to provide a channel 188 that accommodates the drive screw 166 when the device 150 is in the collapsed state. Although not shown, the distal members 154 are similarly constructed and interact with each other in the same manner.

Thus, it can be appreciated that, in the same manner as that described above with respect to the device 100, the combined cross-sectional profile of the proximal members 152, and the combined cross-sectional profile of the distal members 154, are reduced when the device 150 is placed in the collapsed state, yet the shear strength of each member 152/154 is not substantially reduced when the device 150 is placed in the deployed state.

Figure 14:
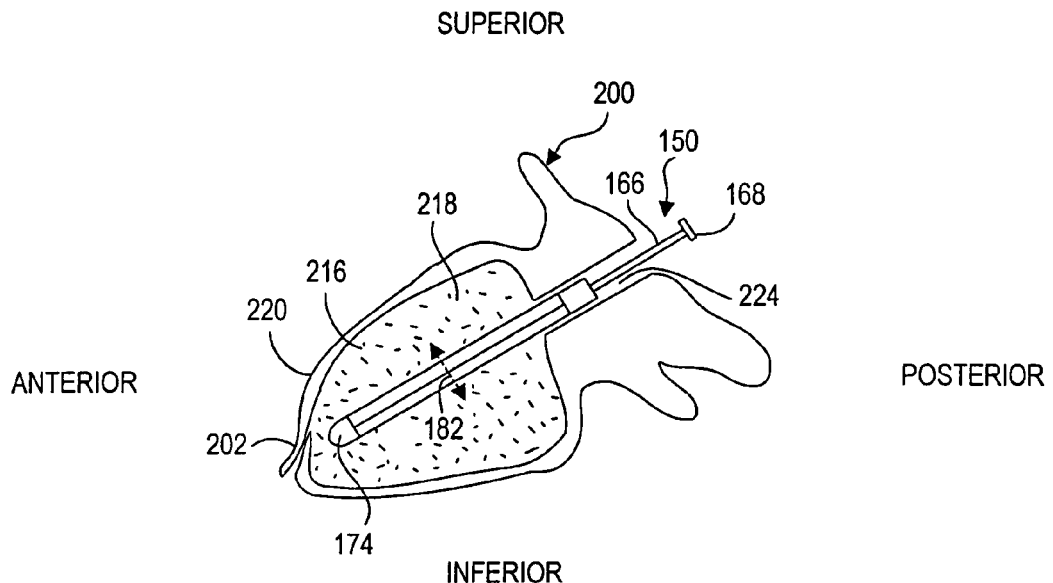
FIGS. 14 and 15 are lateral views of a method of using the device of FIG. 10 to treat a vertebral compression fracture.
Figure 15:
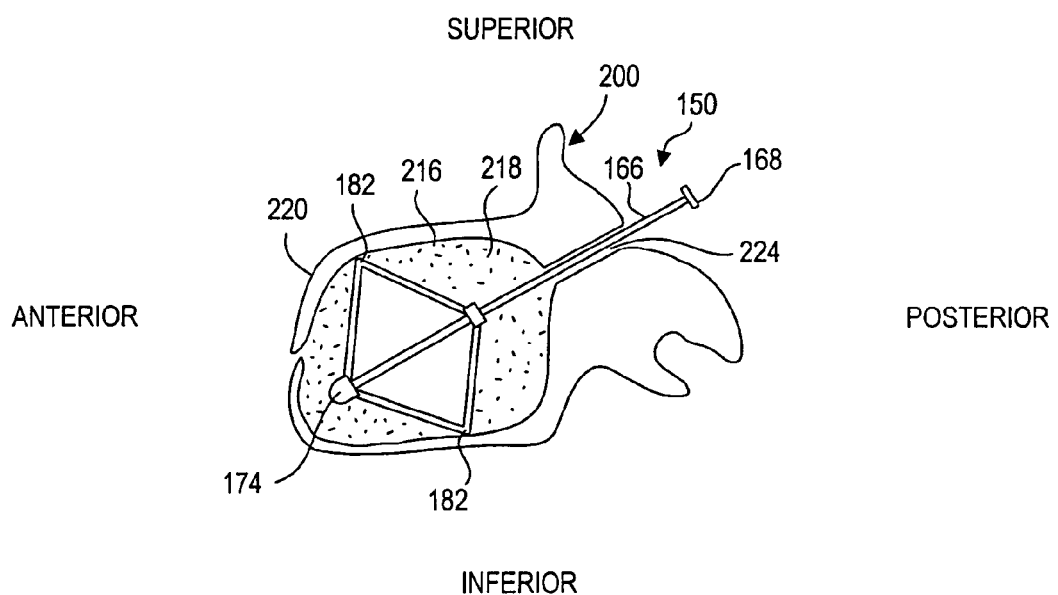

Referring now to FIGS. 14 and 15, a method of using the device 150 to treat a compression fracture 202 within a vertebra 200 will now be described. First, as previously described with respect to FIGS. 7A and 7B, the physician accesses the interior of the vertebral body 216 by boring a channel or passage 224 into the vertebra 200. Once access to the cancellous bone 218 in the vertebral body 216 has been achieved, the physician introduces the device 150 through the passage 224 and into the cancellous bone 218, in the collapsed state, as illustrated in FIG. 14. The spherical cap 174 of the device 150 is preferably placed adjacent the anterior of the vertebral body 216 in order to provide maximum leverage when reducing the fracture 202. The device 150 is oriented, such that expansion of the central hinge points 182 will be in the direction perpendicular to the superior and inferior sides of the vertebra 200.

After proper orientation, the physician places the device 150 in the deployed state by rotating the drive screw 166, e.g., by engaging the drive coupling 168 with a driver (not shown), thereby disengaging the ribs 186 of the proximal members 152 and the ribs 186 of the distal members 154 from each other, and displacing the central hinge points 182 away from each other. As a result, movement of the central hinge points 182 in opposite directions will in turn compress the cancellous bone 218 against the cortical bone 220, thereby displacing the superior and inferior sides of the vertebra 200 in opposite directions to reduce the compression fracture 202, as illustrated in FIG. 15. As previously stated, initial movement of the superior and inferior sides of the vertebra 200 will depend upon the nature and age of the compression fracture 202.

The physician can optionally place the device 150 back in the collapsed state or partially collapsed state if the device 150 needs to be readjusted or reoriented within the vertebral body 216. This can be accomplished by rotating the drive screw 166 in the other direction, thereby displacing the central hinge points 182 back towards each other.

Thus, it can be appreciated that the provision of ribs 186 on the members 152/154 allows the device 150 to be collapsed enough to be introduced through the small passage 224, yet maintain the shear strength necessary to reduce the compression fracture 202.

After reduction of the compression fracture 202 has been completed, the device 150 can be removed from the vertebral body 216, and a therapeutic medium can be introduced through the passage 224 into the void created by displacing the cancellous bone 218 against the cortical bone 220. The cured therapeutic medium will ultimately provide increased structural integrity for the vertebra 200. Alternatively, rather than removing the entire device 150 from the vertebral body 216, the device 150 can be left within the vertebral body 216, while the therapeutic medium is introduced into the vertebral body 216 through another passage. After the therapeutic medium has cured, the proximal end of the drive 164 can then be sheared off, and the channel 224 filled with bone cement.

Figure 16:
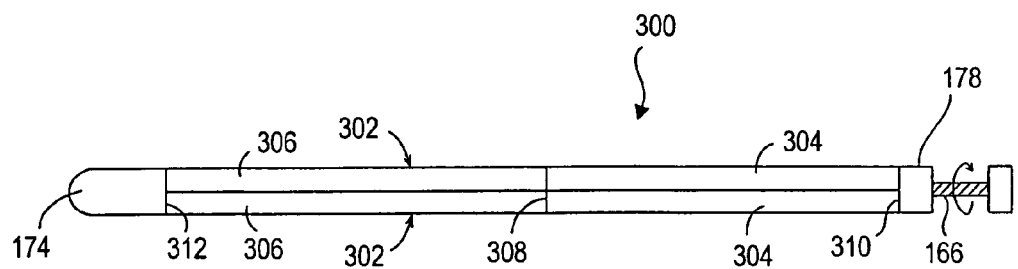
FIG. 16 is a plan view of a vertebral compression fracture reduction device constructed in accordance with still another preferred embodiment of the present inventions, wherein the device is particularly shown in a collapsed state.
Figure 17:
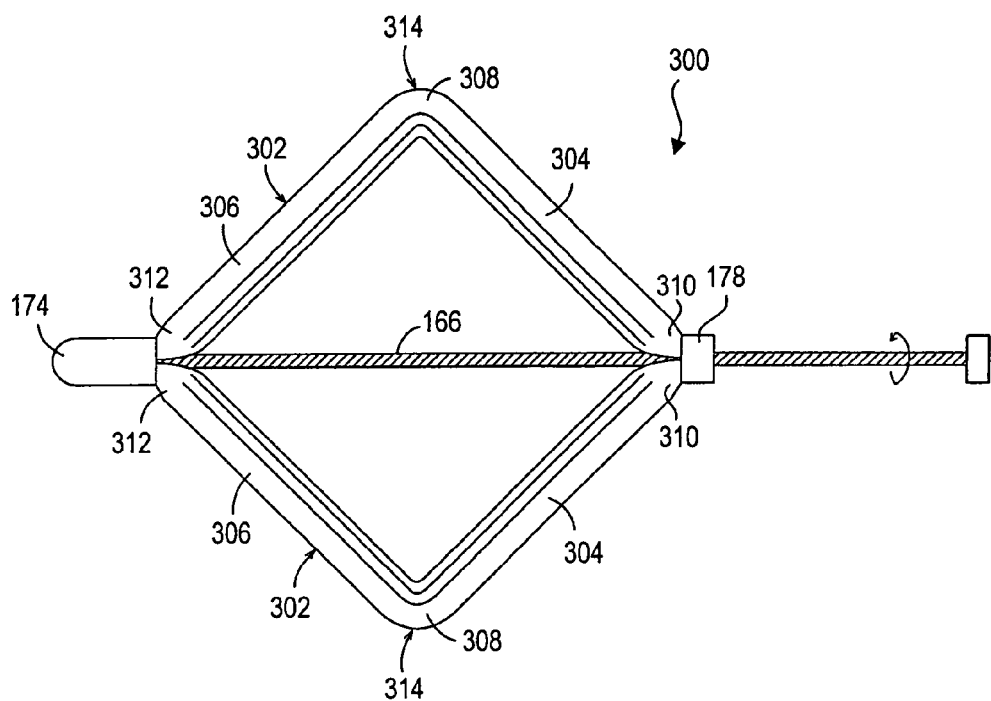
FIG. 17 is a plan view of the device of FIG. 16, wherein the device is particularly shown in a deployed state.

It should be noted that any number of the hinges 156, 176, and 180 of the device 150 can be replaced with "living" hinges, it which case, a corresponding proximal member 152 and distal member 154 would be replaced with a single member that is directly coupled between the spherical cap 174 and nut 178. For example, FIGS. 16 and 17 illustrate a bone fracture reduction device 300 that is similar to the device 150 with the exception that it uses living hinges (i.e., portions where the members are bent or deformed). In particular, the device 300 comprises a pair of rigid members 302 that are formed between the distal spherical cap 174 and the nut 178. Each rigid member 302 comprises a proximal portion 304, a distal portion 306, an intermediate living hinge 308 formed between the proximal and distal portions 304 and 306, a proximal living hinge 310 formed between the proximal portion 304 and the nut 178, and a distal living hinge 312 formed between the distal portion 306 and the spherical cap 174.

In response to distal displacement of the nut 178 relative to the spherical cap 174, the hinging action of the intermediate hinge 308, proximal hinge 310, and distal hinge 312 (i.e., bending or deformation of the members 302) will cause the proximal and distal portions 304 and 306 of each member 302 to move towards each other—in effect collapsing upon each other, which will then cause the distal ends of the proximal portions 304 and the proximal ends of the distal portions 306 to move outward (i.e., away from the drive screw 166) at central hinge points 314, thereby placing the device 300 in its deployed state (FIG. 17). In contrast, in response to proximal displacement of the nut 178 relative to the spherical cap 174, the hinging action of the intermediate hinge 308, proximal hinge 310, and distal hinge 312 will cause the proximal portions 304 and the distal portions 306 to move away from each other at the central hinge points 314, which will then cause the distal ends of the proximal portions 304 and the proximal ends of the distal portions 306 to move inward (i.e., towards the drive screw 166), thereby placing the device 300 in its collapsed state (FIG. 16).

Like with the previously described members of the device 150, the members 302 of the device 300 are specially designed, such that they can be introduced through smaller channels within the vertebra 200 without significant loss of shear strength in the direction of their movement. That is, the members 302 have ribs similar to the ribs 186 illustrated in FIGS. 12 and 13. The device 300 can be used to reduce a vertebral compression fracture in the same manner as that described above with respect to FIGS. 14 and 15, and will thus, not be expressly described herein for purposes of brevity.

Figure 18:
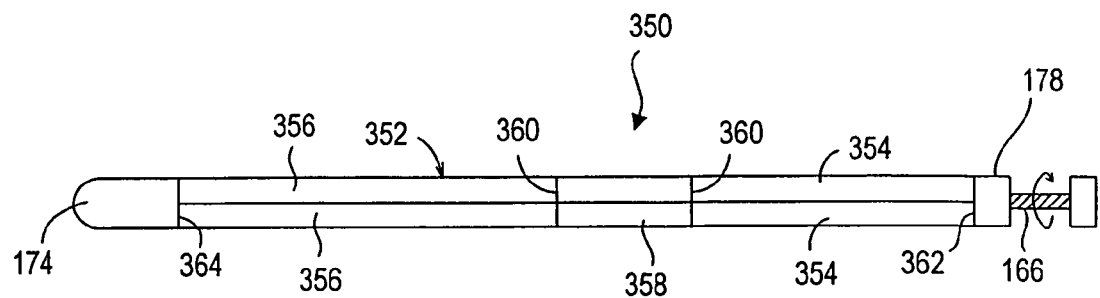
FIG. 18 is a plan view of a vertebral compression fracture reduction device constructed in accordance with yet another preferred embodiment of the present inventions, wherein the device is particularly shown in a collapsed state.
Figure 19:
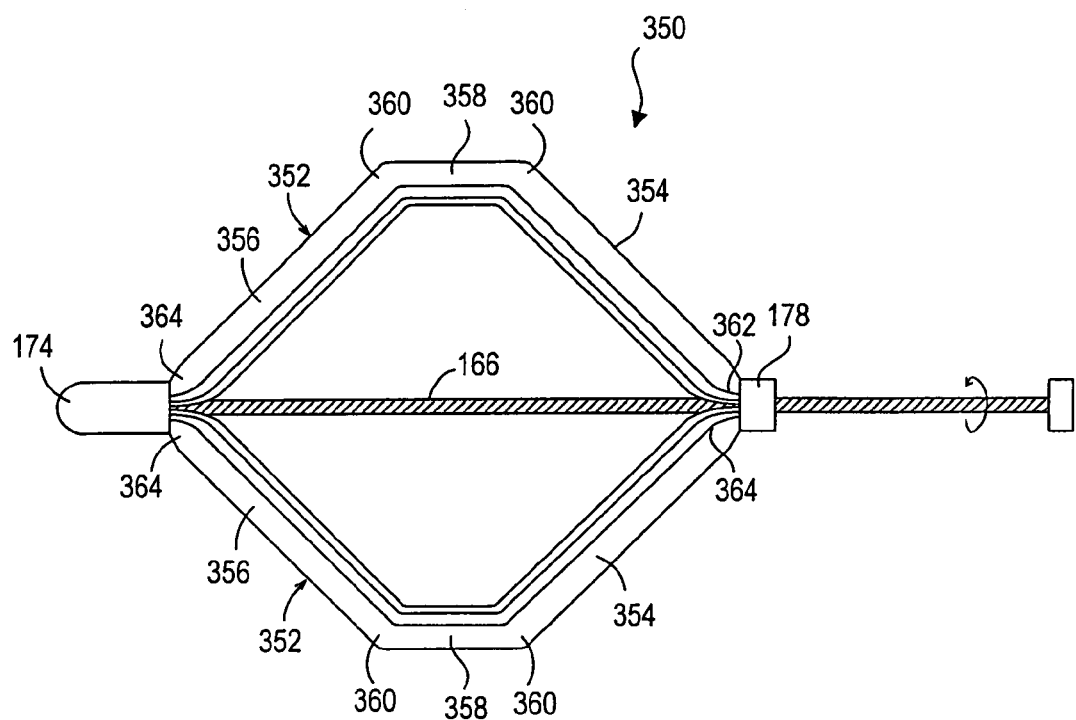
FIG. 19 is a plan view of the device of FIG. 18, wherein the device is particularly shown in a deployed state.

Referring now to FIGS. 18 and 19, another bone fracture reduction device 350 is illustrated. The device 350 is similar to the previously described device 300 with the exception that it includes a pair of central supports as opposed to central hinge points. In particular, the device 350 comprises a pair of rigid members 352 that are formed between the distal spherical cap 174 and the nut 178. Each member 352 comprises a proximal portion 354, a distal portion 356, and a central portion 358. Each member 352 also comprises two intermediate living hinges 360 between central portion 358 and the respective proximal and distal portions 354 and 356, a proximal living hinge 362 formed between the proximal portion 354 and the nut 178, and a distal living hinge 364 formed between the distal portion 356 and the spherical cap 174.

In response to distal displacement of the nut 178 relative to the spherical cap 174, the hinging action of the intermediate hinges 360, proximal hinge 362, and distal hinges 364 will cause the proximal and distal portions 354 and 356 of each member 302 to move towards each other—in effect collapsing upon each other, which will then cause the central portions 358 to move outward (i.e., away from the drive screw 166), thereby placing the device 350 in its deployed state (FIG. 19). In contrast, in response to proximal displacement of the nut 178 relative to the spherical cap 174, the hinging action of the intermediate hinges 360, proximal hinges 362, and distal hinges 364 will cause the proximal portions 354 and the distal portions 356 to move away from each other, which will then cause the central portions 358 to move inward (i.e., towards the drive screw 166), thereby placing the device 350 in its collapsed state (FIG. 18).

Like with the previously described members of the device 150, the members 352 of the device 350 are specially designed, such that they can be introduced through smaller channels within the vertebra 200 without significant loss of shear strength in the direction of their movement. That is, the members 352 have ribs similar to the ribs 186 illustrated in FIGS. 12 and 13. The device 350 can be used to reduce a vertebral compression fracture in the same manner as that described above with respect to FIGS. 14 and 15, with the exception that the central portions 358 engages a greater area of the bone structure than does the central hinge points 182, thereby providing a greater control in reducing the fracture, as well as minimizing damage to the inferior and superior sides of the vertebra 200.

Figure 20:
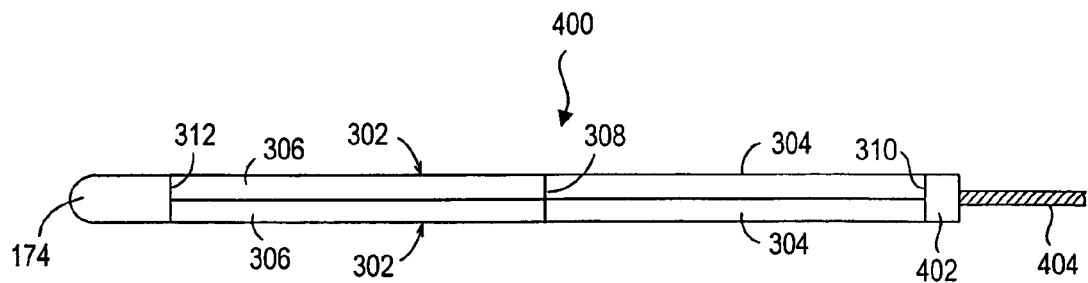
FIG. 20 is a plan view of a vertebral compression fracture reduction device constructed in accordance with yet another preferred embodiment of the present inventions, wherein the device is particularly shown in a collapsed state.
Figure 21:
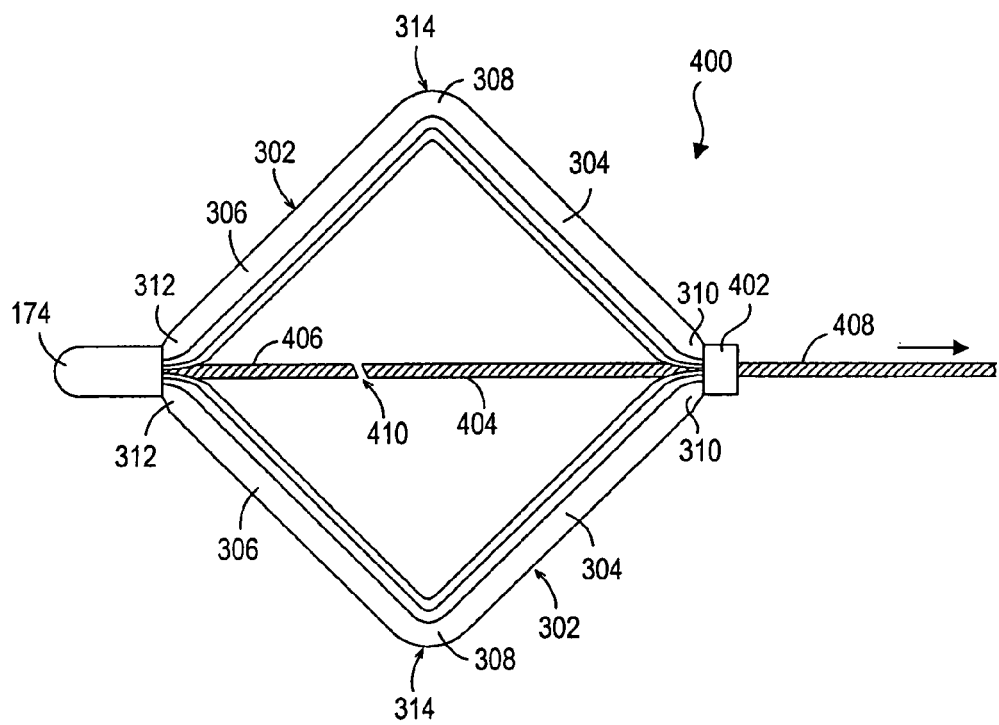
FIG. 21 is a plan view of the device of FIG. 20, wherein the device is particularly shown in a deployed state.

Referring now to FIGS. 20 and 21, another bone fracture reduction device 400 is illustrated. The device 400 is similar to the previously described device 300 with the exception that it includes a shear rod or wire, rather than a drive screw. In particular, the device 400 comprises an annular ring 402, and a shear wire 404 that has a distal end 406 that is mounted within the spherical cap 174 (e.g., by soldering, glue, welding, or other suitable junction method), and a proximal end 408 that extends through the aperture (not shown) of the annular ring 402.

Proximal movement of the shear wire 404 relative to the annular ring 402 (e.g., by pulling the shear wire 404) will longitudinally displace the spherical cap 174 in the proximal direction. In response to proximal displacement of the spherical cap 174 relative to the annular ring 402, the hinging action of the intermediate hinge 308, proximal hinge 310, and distal hinge 312 will cause the proximal and distal portions 304 and 306 of each member 302 to bend or deform towards each other—in effect collapsing upon each other, which will then cause the distal ends of the proximal portions 304 and the proximal ends of the distal portions 306 to move outward (i.e., away from the shear wire 404) at central hinge points 314, thereby placing the device 400 in its deployed state (FIG. 21). The shear wire 404 has a weakened region 410 near it distal end 406 that breaks once a predetermined tensile force has been exerted on the shear wire 404. In this manner, once the device 400 has been fully deployed, the tensile force on the shear wire 404 will increase causing the shear wire 404 to break. The device 400 will remain in its deployed state by virtue of the natural resistance of the members 304 to return to their undeformed state. Alternatively, the shear wire 404 can be designed, such that the weakened region 410 is inside or just proximal to the annular ring 402 when the device 400 is fully deployed. In this case, the portion of the shear wire 404 just distal to the weakened region 410 can be designed, such that it wedges into the annular ring 402 when the shear wire 404 breaks.

Notably, once the device 400 has been placed in the deployed state, it cannot be normally placed back into the collapsed state. If the shear wire 404 is replaced with a shear rod that exhibits the necessary column strength, however, the device 400 can be placed back into the collapsed state if the shear rod has not yet broken. In this case, the shear rod may be distally displaced in order to cause the distal ends of the proximal portions 304 of the members 302 and the proximal ends of the distal portions 306 of the members 304 to move inward (i.e., toward the shear rod) at central hinge points 314, thereby placing the device 400 in the collapsed state (FIG. 20).

The device 400 can be used to reduce a vertebral compression fracture in the same manner as that described above with respect to FIGS. 14 and 15, with the exception that the shear wire 404 is pulled in order to deploy the device 400. In addition, the shear wire 404 automatically breaks off after deployment of the device 400, whereas in the former case, an affirmative step must be taken in order to break the drive screw 166 off.

Figure 22:
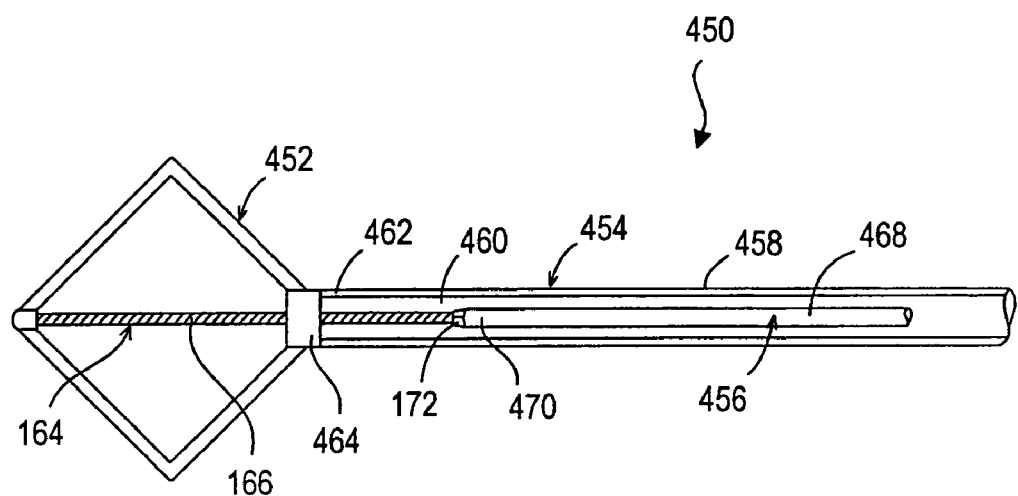
FIG. 22 is a plan view of a vertebral compression fracture reduction assembly constructed in accordance with yet another preferred embodiment of the present inventions.

It should be noted that during deployment, the previously described devices can be positioned and stabilized using any of a variety of mechanisms. For example, FIG. 22 illustrates a bone fracture treatment assembly 450 that generally comprises a bone fracture reduction device 452, a cannula 454 that is configured to stabilize and control the position of the device 452, and a screw driver 456 for actuating deployment of the device 452.

The cannula 454 comprises a shaft 458 with a distal tip 462, and a lumen 460 extending through the cannula shaft 458. To facilitate control of the device 452, the cannula shaft 458 is preferably stiff (e.g., it can be composed of a stiff material, or reinforced with a coating or a coil to control the amount of flexing). The materials used in constructing the cannula shaft 458 may comprise any of a wide variety of biocompatible materials. In a preferred embodiment, a radiopaque material, such as metal (e.g., stainless steel, titanium alloys, or cobalt alloys) or a polymer (e.g., ultra high molecular weight polyethylene) may be used, as is well known in the art.

The outer diameter of the cannula shaft 458 is preferably less than ½ inch, although other dimensions for the outer diameter may also be appropriate, depending on the particular application or clinical procedure. The cannula lumen 460 should have a diameter so as to allow movement of the screw driver 456 therein. In the illustrated embodiment, the profile of the cannula lumen 460 is circular, but can be other shapes as well.

Figure 23:
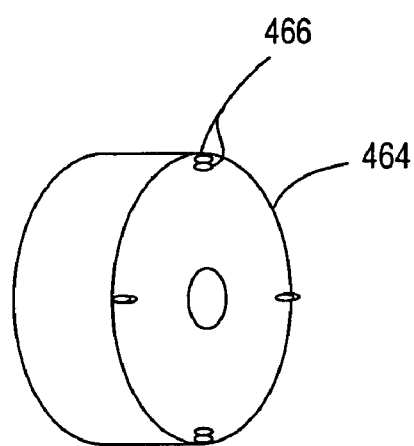
FIG. 23 is a perspective view of a nut used in the assembly of FIG. 22.

The device 452 is similar to the previously described device 150 with the exception that it comprises a nut 464 that is specifically configured for engaging the cannula 454. In particular, the nut 464 comprises clasps 466 (shown in FIG. 23) for grasping the distal tip 462 of the cannula 454. For example, four clasps 464 can be provided for respectively grasping the top, bottom, left side, and right side of the cannula tip. The screw driver 456 comprises a shaft 468 and a distal tip 470 that is configured for engaging the drive coupling 172 of the drive 164. For example, if the drive coupling 172 is a hex head, the distal tip 470 of the screw driver 456 can be a hex socket. If the drive coupling 172 has a slot, the distal tip 470 of the screw driver 456 can be a flat flange.

Figure 24:
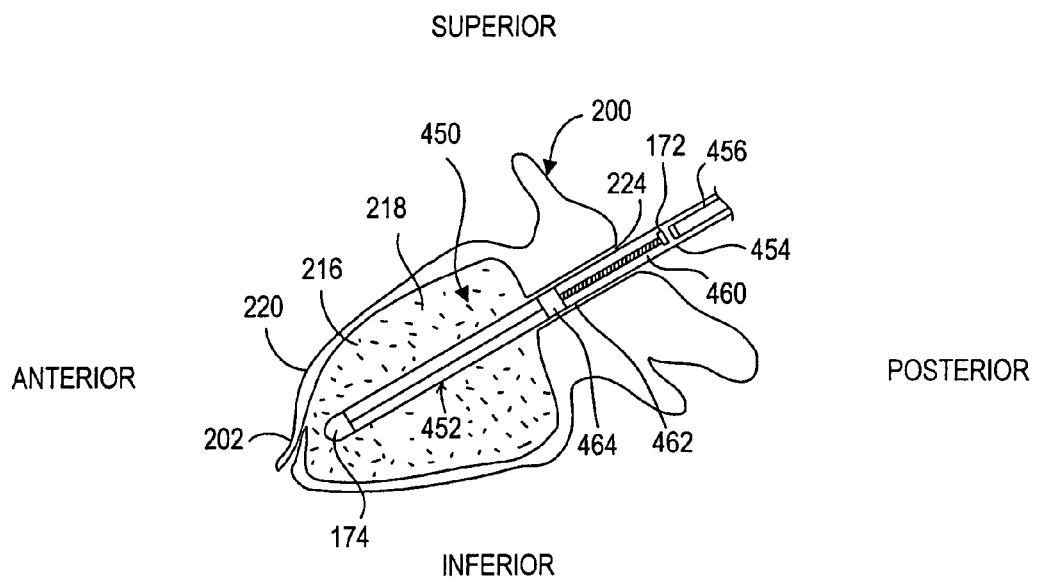
FIGS. 24 and 25 are lateral views of a method of using the assembly of FIG. 23 to treat a vertebral compression fracture.
Figure 25:
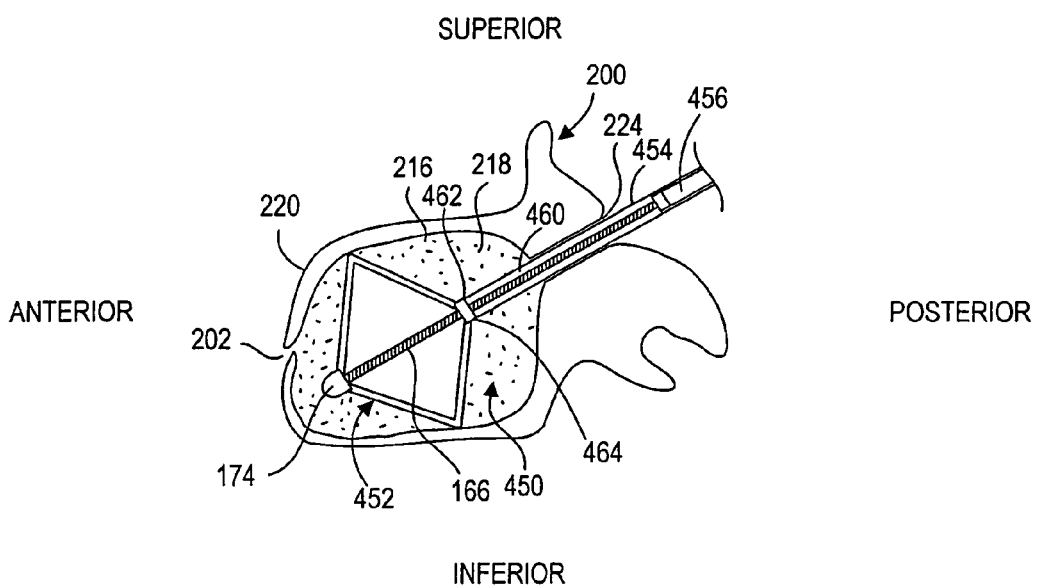

Referring now to FIGS. 24 and 25, a method of using the assembly 450 to treat a compression fracture 202 within a vertebra 200 will now be described. First, as previously described with respect to FIGS. 7A and 7B, the physician accesses the interior of the vertebral body 216 by boring a channel or passage 224 into the vertebra 200. Once access to the cancellous bone 218 in the vertebral body 216 has been accessed, the physician introduces the device 452 through the passage 224 and into the cancellous bone 218, in the collapsed state, in the same manner as the device 150 was introduced into the cancellous bone 218 illustrated in FIG. 14.

The cannula 454, preferably with the screw driver 456 disposed within the cannula lumen 460, is then introduced through the passage 224 into engagement with the device 452, as illustrated in FIG. 24. In particular, the cannula 454 is manipulated, such that the drive coupling 172 of the device 452 is received into the cannula lumen 460, and the clasps 466 (shown in FIG. 23) of the nut 464 receive the distal tip 462 of the cannula shaft 458. The device 452 is then properly oriented and positioned by moving the cannula 454. For example, the device 452 can be moved, such that the spherical cap 174 is placed adjacent to the anterior side of the vertebra 200. Once properly positioned, the screw driver 456 can be adjusted, such that its distal tip 462 engages the drive coupling 172, and then rotated to deploy the device 452, thereby reducing the compression fracture 202, as illustrated in FIG. 25. During deployment of the device 452, distal pressure can be maintained on the cannula 454, so that the nut 464 moves distally towards the spherical cap 174, rather than the spherical cap 174 moving proximally towards the nut 464. In this manner, deployment of the device 452 within the anterior portion of the vertebral body 216 is ensured. In addition, because the nut 464 is fully engaged with the distal tip 462 of the cannula shaft 458, rotation of the device 452 is prevented while the drive screw 166 is being rotated.

After reduction of the compression fracture 202 has been completed, the cannula 454 is disengaged with the device 452. As previously described, the device 452 can be removed from or left within the vertebral body 216, after which a therapeutic medium can be introduced through the passage 224 into vertebral body 216.

It should be noted that all of the biocompatible members described herein can be composed of a semi-rigid, rather than a rigid, material. For the purposes of this specification, a semi-rigid member is one that laterally flexes in the presence of the force required to reduce the compression fracture of the bone structure in which the member is intended to be introduced. Providing semi-rigid members has the advantage of distributing the stress along the bone surface that the members contact, thereby minimizing the risk that a member will puncture or fracture the wall of the bone structure at areas other than the original fracture site.

It should also be noted that the use of the devices described herein are not limited to the reduction of a bone fracture, but can also be used for stabilizing adjacent bone structures, e.g., vertebrae, with or without additional material to further stabilize the bone structures.

Although particular embodiments of the present invention have been shown and described, it should be understood that the above discussion is not intended to limit the present invention to these embodiments. It will be obvious to those skilled in the art that various changes and modifications may be made without departing from the spirit and scope of the present invention. Thus, the present invention is intended to cover alternatives, modifications, and equivalents that may fall within the spirit and scope of the present invention as defined by the claims.

What is claimed is:

1. A device for treating a bone structure, comprising:
a first biocompatible rigid or semi-rigid member having a proximal portion and a distal portion, the distal portion having a first plurality of ribs extending therefrom;
a second biocompatible rigid or semi-rigid member having a proximal portion and a distal portion, the distal portion having a second plurality of ribs extending therefrom;
wherein the first and second members have a combined cross-sectional circular profile, and each of the first and second members has a respective individual cross-sectional arcuate profile, the combined cross-sectional profile having a radius that is substantially equal to a radius of curvature of the individual cross-sectional profile, and wherein the device is configured to be placed in a collapsed state by engaging the first and second pluralities of ribs in an interposed arrangement with the respective proximal portions of the first and second members spaced apart from each other, and in a deployed state by disengaging the first and second pluralities of ribs, with the respective proximal portions of the first and second members moved towards each other.

2. A method of treating a bone structure having opposing sides and a compression fracture therebetween, the method comprising:
providing a device with first and second members, each of which has a proximal portion and distal portion and a plurality of ribs extending from the respective distal portions;
placing the device in a collapsed state by engaging the ribs of the respective first and second members in an interposed arrangement with the respective proximal portions of the first and second members spaced apart from each other;
introducing the device within the bone structure while in the collapsed state;
placing the device in a deployed state by disengaging the ribs of the respective first and second members, wherein the respective proximal portions of the first and second members moved towards each other, wherein the distal portions of the first and second members move in opposite directions to displace the opposing sides of the bone structure in opposite directions.

3. The method of claim 2, wherein the device is placed in the respective collapsed and deployed states by hinging the first and second members relative to each other.

4. The method of claim 2, wherein the first and second pluralities of ribs are flutes.

5. The method of claim 2, wherein the first and second members have a combined cross-sectional circular profile, and each of the first and second members has a respective individual cross-sectional arcuate profile, the combined cross-sectional profile having a radius that is substantially equal to a radius of curvature of the individual cross-sectional profile.

6. The method of claim 2, wherein the bone structure is a vertebral body.

7. The method of claim 2, wherein the device is deployed until the compression fracture has been completely reduced.

8. The method of claim 2, further comprising introducing treatment medium into the bone structure after deployment of the device within the bone structure.

9. The method of claim 2, further comprising stabilizing the bone fracture.

* * * * *

UNITED STATES PATENT AND TRADEMARK OFFICE
CERTIFICATE OF CORRECTION

| | | |
|---|---|---|
| PATENT NO. | : 7,513,900 B2 | Page 1 of 1 |
| APPLICATION NO. | : 10/674723 | |
| DATED | : April 7, 2009 | |
| INVENTOR(S) | : Harold F. Carrison et al. | |

It is certified that error appears in the above-identified patent and that said Letters Patent is hereby corrected as shown below:

In the Claims:

In Claim 2, column 14, line 24, please delete "wherein" and insert therefore -- with --.

Signed and Sealed this

Second Day of June, 2009

JOHN DOLL
*Acting Director of the United States Patent and Trademark Office*